United States Patent
Flohr

(10) Patent No.: US 8,548,116 B2
(45) Date of Patent: Oct. 1, 2013

(54) METHOD FOR SCANNING A HEART WITH A DUAL-SOURCE CT DEVICE AND EMBODIMENT OF A DUAL-SOURCE CT DEVICE

(75) Inventor: Thomas Flohr, Uehlfeld (DE)

(73) Assignee: Siemens Aktiengesellschaft, Munich (DE)

( * ) Notice: Subject to any disclaimer, the term of this patent is extended or adjusted under 35 U.S.C. 154(b) by 102 days.

(21) Appl. No.: 13/249,321

(22) Filed: Sep. 30, 2011

(65) Prior Publication Data
US 2012/0082290 A1 Apr. 5, 2012

(30) Foreign Application Priority Data
Sep. 30, 2010 (DE) .......................... 10 2010 041 774

(51) Int. Cl.
*A61B 6/00* (2006.01)

(52) U.S. Cl.
USPC .................................................. 378/9; 378/8

(58) Field of Classification Search
USPC ......................................................... 378/8, 9
See application file for complete search history.

(56) References Cited

U.S. PATENT DOCUMENTS

| | | |
|---|---|---|
| 2003/0076920 A1 | 4/2003 | Shinno et al. |
| 2004/0213371 A1* | 10/2004 | Bruder et al. ...................... 378/9 |
| 2005/0089134 A1* | 4/2005 | Bruder et al. ...................... 378/9 |
| 2005/0111622 A1* | 5/2005 | Bruder et al. .................... 378/95 |
| 2005/0111623 A1* | 5/2005 | Bruder et al. .................... 378/95 |
| 2007/0025499 A1* | 2/2007 | Bruder et al. ...................... 378/9 |
| 2007/0098136 A1* | 5/2007 | Lutz ................................... 378/9 |
| 2007/0280407 A1* | 12/2007 | Kunze et al. ...................... 378/4 |
| 2012/0082289 A1* | 4/2012 | Flohr ................................. 378/8 |

OTHER PUBLICATIONS

German Priority Application No. 10 2010 041 774.2 dated Sep. 30, 2010 (not yet published).
German Office Action for German Application No. 10 2010 041 774.2 dated Apr. 6, 2011.

* cited by examiner

*Primary Examiner* — Alexander H Taningco
(74) *Attorney, Agent, or Firm* — Harness, Dickey & Pierce, P.L.C.

(57) ABSTRACT

A method is disclosed for CT scanning a heart with a dual-source CT device including detectors of different widths in a system axis direction and for reconstruction of tomographic image data. In at least one embodiment, at least two circular scans are performed at different z positions and the spacing in the z direction is chosen such that at least two first scan zones are produced which are scanned by way of a circular scan with two detectors and at least one second scan zone is produced which is scanned twice by one detector in two successive circular scans, wherein a dual-source reconstruction is performed in the first scan zones and a two-segment reconstruction is performed in the at least one second scan zone and finally a common tomographic image data set is produced. Further, at least one embodiment is directed to a dual-source CT device in which the detectors have different widths in the system axis direction.

14 Claims, 2 Drawing Sheets

METHOD FOR SCANNING A HEART WITH A DUAL-SOURCE CT DEVICE AND EMBODIMENT OF A DUAL-SOURCE CT DEVICE

PRIORITY STATEMENT

The present application hereby claims priority under 35 U.S.C. §119 on German patent application number DE 10 2010 041 774.2 filed Sep. 30, 2010, the entire contents of which are hereby incorporated herein by reference.

FIELD

At least one embodiment of the invention generally relates to a method for CT scanning a heart with a dual-source CT device having two focus-detector systems with detectors of different widths in the system axis direction and to the reconstruction of tomographic image data. At least one embodiment of the invention also generally relates to a dual-source CT device with two focus-detector systems arranged on a gantry so as to be angularly offset and/or to a computer system with a program memory for program data by which, during operation, the dual-source CT device is controlled and CT image data is reconstructed.

BACKGROUND

A method and a corresponding dual-source CT device for performing the method is generally known and is often used if an optimally high time resolution is desired during a CT scan, for example in order to create tomographic images of a beating heart.

The ECG-triggered sequence mode is a very common, dose-efficient technique for examining the heart by way of a dual-source CT device. With this examination technique the ECG signal from the patient is used to trigger axial scans without couch movement using two measurement systems in a user-selectable cardiac phase of the patient, preferably in the low-movement end-diastolic phase. Following such an axial scan the patient couch moves to the next examination position where, again triggered by the patient's ECG, the next axial scan is performed. The examination volume covered in a single axial scan roughly corresponds to the width of the two detectors (of equal width according to the prior art) in the rotation center of the CT system, reduced by an overlap region of about 10% which is necessary for the image reconstruction. The width of the detector is therefore measured in the system axis direction or also the z direction of the CT system, i.e. in the longitudinal direction of the patient.

With a dual-source CT device having two detectors with for example 64×0.6 mm collimation each, corresponding to a width in the z direction of 38.4 mm, the covered volume per axial scan is about 35 mm. For examination of the entire heart volume of about 12 cm extension in the z direction, four axial scans as an example are required with such a device. The time resolution of the images produced with this scan mode is therefore about a quarter of the rotation time of the dual-source CT device when the simultaneously recorded data of the two detectors is taken into account.

It is desirable to reduce the number of individual scans for imaging the heart volume, i.e. to have to perform for example only two individual axial scans in future instead of four. The total examination time is reduced as a result. Fewer cardiac periods would therefore contribute to the image and the risk of image quality problems, for example due to the changing contrast agent concentration throughout the overall examination period or the changing heart rate of the patient, would be lower.

SUMMARY

The inventors have discovered that, according to the current prior art, single-source CT devices are being fitted with ever wider detectors which, for example, cover 16 cm in the length direction of the patient (Toshiba Aquilion ONE®) or 8 cm in the length direction of the patient (Philips ICT®). They have further discovered that these systems have the drawback of poorer time resolution than dual-source CT devices. Whereas with dual-source CT devices the time resolution is about a quarter of the rotation time due to the two measurement systems offset by about 90°, in the case of the 180° scans considered here it is about half the rotation time with single-source CT devices.

In cardio CT, what are known as multi-segment reconstructions are known which improve the time resolution by using data from two or more successive cardiac periods. However, a CT device with an 8 cm wide detector must scan the same z position in two successive cardiac cycles in order to cover the entire heart with a two-segment reconstruction, which in the best case achieves a dual-source CT equivalent time resolution of about a quarter of the rotation time, such that, overall, two axial scans have to be performed at each couch position and consequently once again at least four cardiac periods contribute to the image of the overall heart volume.

If in the case of a dual-source CT device the number of axial scans for covering the heart volume is to be reduced, then according to the prior art it is necessary to make the two detectors wider in the z direction, i.e. for example to use two detectors each with about 8 cm detector width instead of each with about 4 cm detector width. With such a device it would be possible to image the entire heart volume with just two ECG-triggered axial scans using data from only two cardiac periods with the best possible time resolution of about a quarter of the rotation time. However, such a device would be very complex technically (for example transverse scattering problems), and the costs for two wide detectors would be very high.

In at least one embodiment of the invention, a scanning method and a dual-source CT device are disclosed in which, with the lowest constructional complexity and with a minimum number of sequential cardio scans, an optimally wide region of the heart can be scanned in the system axis direction, while at the same time an optimum time resolution with few artifacts is achieved in the important regions.

Advantageous developments of the invention are the subject matter of subordinate claims.

In at least one embodiment, the inventor proposes an ECG-triggered sequence recording method for a dual-source CT device which is equipped with two detectors of different widths in the z direction. If the detectors are called A and B, then detector B can preferably be implemented so as to be twice as wide as detector A. With such a device, the z width for example of the detector A could be left at $B_1=64\times0.6$ mm, while detector B is enlarged to a z width of $B_2=128\times0.6$ mm. With this arrangement, with two detectors A and B of widths $B_1$ and $B_2$, where $B_2>B_1$, it is possible to cover the entire heart with, for example, two overlapping axial scans. To improve the time resolution in the z regions of the examination object which are covered by both detectors A and B simultaneously, a dual-source CT image reconstruction is performed using the minimum data volume of about a quarter revolution per detector. The time resolution is about a quarter of the rotation time in this case.

In the overlap region between the two axial scans there is essentially only data present from the wider detector, of the detector B in the example here, although this data originates from two successive cardiac periods. A two-segment reconstruction is performed here in order to improve the time resolution. A heart-rate-dependent optimization of the rotation time of the scanner is sometimes helpful for this purpose.

It is only at the start and end of the scan volume that there is exclusively data from the wider detector from just one cardiac period. No better time resolution than about half the rotation time is possible here. However, in these regions this is not critical because these usually constitute a certain "safety zone" which is scanned in order to image the heart completely in any case but which is sufficiently far removed from the moving parts of the heart that are actually of interest, for example the right coronary artery.

According to at least one embodiment of the proposed method the finished CT image data set of a heart is therefore made up of a combination of image data from a dual-source CT image reconstruction with simultaneously recorded detector data from the dual-source CT device, a two-segment-reconstruction with successively recorded detector data from different positionings of the detector and from two different, usually not immediately successive cardiac cycles, and optionally at the edge—relative to the z direction—also from CT image data from a reconstruction from detector data of the same detector without a change in z position from possibly a plurality of successive cardiac cycles.

According to the above-described basic concept, the inventor proposes a method, in at least one embodiment, for CT scanning a heart with a dual-source CT device having two focus-detector systems with detectors of different widths in the system axis direction and reconstruction of tomographic image data, which method comprises the following steps of:

performing at least two circular scans at different z positions, the spacing in the z direction being chosen such that at least two first scan zones are produced which are scanned by way of a circular scan with two detectors and at least one second scan zone is produced which is scanned twice in two successive circular scans by one detector, reconstructing first tomographic image data in the first scan zones using absorption data from the narrower and the wider (=dual-source reconstruction), reconstructing second image data in the at least one second scan zone from absorption data of the wider detector from two successive circular scans at different z positions (=two-segment reconstruction), assembling a common tomographic image data set from at least the first and second image data.

It is advantageous in this connection if the CT scanning is performed with ECG triggering, in particular if only detector data from the resting phase of the heart is used for the reconstruction.

In order to improve at least one embodiment of the inventive method it is also proposed that a rotational speed is chosen as a function of an anticipated heart rate, said rotational speed being time-resolution-optimized with respect to the reconstruction of second image data in the at least one second scan zone from absorption data of the wider detector from two successive circular scans at different z positions.

In at least one embodiment of the method described here, it is particularly favorable if a detector pair is used in which the narrower detector is half as wide as the wider detector, relative to the effective detector surface.

Referred to the system axis direction there may also be one or two marginal scan areas present in which adequate scanning is performed with just one focus-detector system without changing the z position. In this case a reconstruction of an image data set is performed in each case using detector data from a single sequential circular scan and said image data is also added to the common tomographic image data set.

Detectors can also be used which are displaced relative to each other in the system axis direction between two successive circular scans. This avoids the above-described regions in which only single scans are present.

Within the scope of at least one embodiment of the present invention, in addition to the above-described method, the inventor also proposes a dual-source CT device which is equipped with two focus-detector systems arranged on a gantry so as to be angularly offset, wherein the detectors have different widths in the system axis direction and a computer system having a program memory containing program data is provided by which the dual-source CT device is controlled and CT image data reconstructed during operation.

With the dual-source CT device, the two detectors can be arranged on the gantry in such a way that the wider detector projects beyond the narrower detector in the system axis direction to the same extent on either side.

Finally, with the dual-source CT device, program code can preferably also be stored in the memory of the computer, the program code performing at least one embodiment of the above-described inventive method during operation.

Using the recording technology proposed here for a dual-source CT device with two detectors of different width in the z direction it is therefore possible to achieve improved volume coverage in the case of ECG-triggered sequence scans of the heart without both detectors having to be widened and without losing the improved time resolution of a dual-source CT device in important parts of the heart volume. The technology is based on a sequence of time-resolution-optimized dual-source CT reconstructions in the common scan area of the two detectors and two-segment single-source reconstructions in the overlap region of two successive axial scans.

In contrast to single-source CT devices with multi-segment recording technology, in order to improve the time resolution it is not necessary to scan each z position of the heart two or more times in successive cardiac periods, but instead the two-segment reconstruction is only applied in the overlap regions between two successive axial scans. As a result it is possible for example using a dual-source CT device with detectors that are about 8 cm and 4 cm wide in the z direction to visualize the heart with optimized time resolution using data from just two cardiac periods.

BRIEF DESCRIPTION OF THE DRAWINGS

The invention is described in more detail hereinbelow with reference to an example embodiment and with the aid of the figures, with only the features required for an understanding of the invention being shown. The following reference characters are used: 1: dual-source CT device; 2: first X-ray tube; 3: first detector; 4: second X-ray tube; 5: second detector; 6: gantry housing; 7: patient; 8: patient couch; 9: system axis; 10: computer; 11: contrast agent applicator; 12: ECG scan lead; A: detector, B: detector; $Prg_1$ to $Prg_n$: computer programs; V1: characteristic of the time resolution with 0.265 s rotation time; V2: characteristic of the time resolution with 0.285 s rotation time; I: second scan zone; II: first scan zone; III: edge scan area.

In the figures.

DETAILED DESCRIPTION OF THE EXAMPLE EMBODIMENTS

Figure 1:
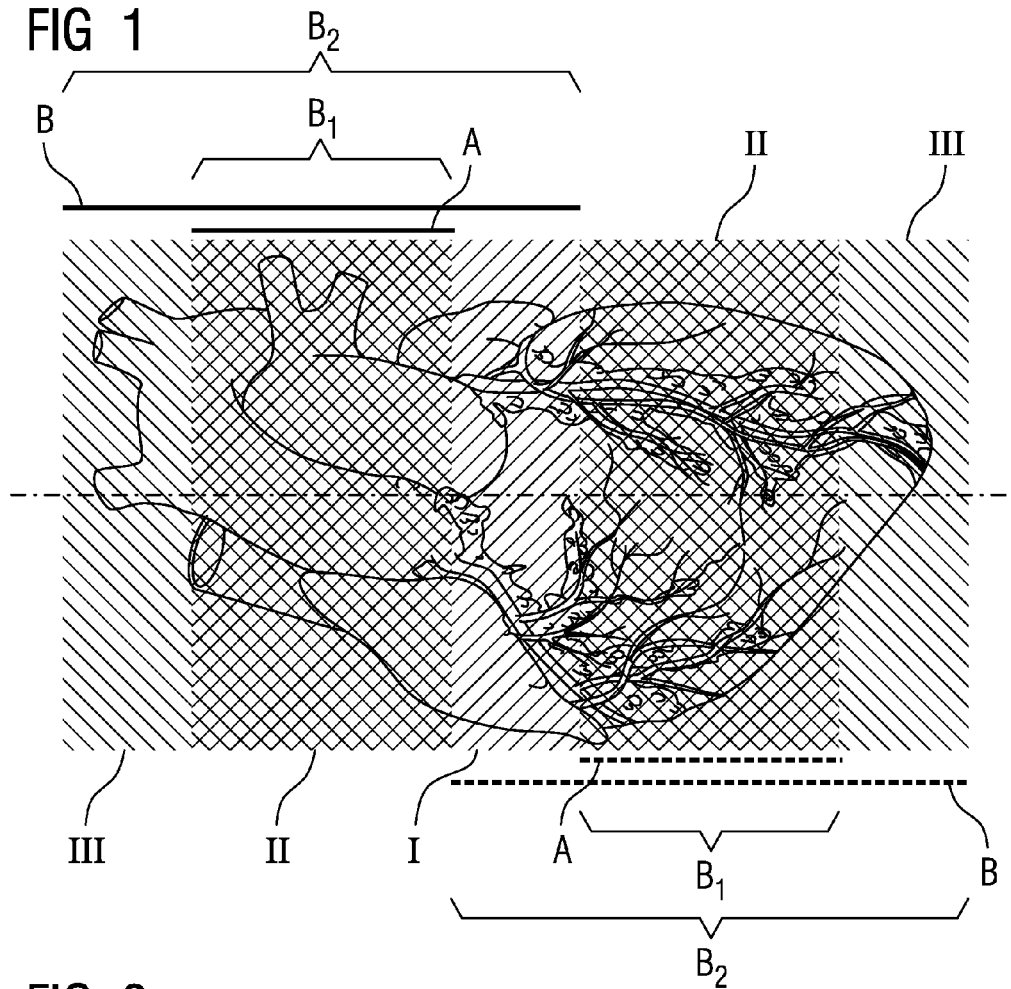
FIG. 1: is a schematic representation of the overlap regions of two detectors of a dual-source CT device according to an embodiment of the invention.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The entire scan range of a cardio CT examination is typically 12-14 cm. On the other hand the z extension of the moving coronary arteries that are of interest is only about 10 cm. In a specific embodiment of a dual-source CT device the inventor proposes equipping said device—as is schematically shown in FIG. 1—with a detector A with 64×0.6 mm collimation, i.e. a total z width of $B_1$=38.4, while the other detector B is significantly widened, for example to 128×0.6 mm collimation with a total z width of $B_2$=76.8 mm. The two detectors A and B overlap in the central region of the detector B over the width $B_1$=38.4 mm. Adjoining said central region, which is scanned simultaneously by both detectors, at each side is a region of width $(B_2-B_1)/2$=19.2 mm, which is only scanned by the wider detector B per axial scan. According to the inventive method, the heart volume is covered by two ECG-triggered axial scans in such a way that the couch offset in the z direction between the two scans is $B_1+(B_2-B_1)/2$ or less, i.e. in this example 38.4 mm+19.2 mm=57.6 mm or less.

A central overlap region I of width $(B_2-B_1)/2$ or more therefore results between the two scans. The detectors A and B represented schematically by solid lines on the left-hand side correspond to the first circular scan, while the detectors represented by broken lines on the right correspond to the z position of the second circular scan. In this specific example the overlap region is 19.2 mm, with data of the wider detector B from both axial scans and consequently from two cardiac periods being available here. In this central overlap region I a two-segment reconstruction is performed from all available data, substantially from detector B, with optimized time resolution.

The achievable time resolution is at best a quarter of the rotation time as a function of the heart rate and the rotation time. If with a larger overlap region there is also data from detector A present, a dual-source reconstruction with optimized time resolution is performed in the affected regions if possible. A region II of width $B_1$, in the specific example with 38.4 mm each on either side, in which data from both detectors A and B from the same cardiac period is available, adjoins the central overlap region of the two axial scans in the z direction on both sides. A dual-source image reconstruction with optimized time resolution is performed here in which the minimum quantity of data from about a quarter revolution each per measurement system is used to attain a time resolution of about a quarter of the rotation time. The entire z region with improved time resolution either from a two-segment reconstruction or from a dual-source reconstruction is therefore $2*B_1+(B_2-B_1)/2$, in the specific example 76.8 mm+19.2 mm=96 mm.

One region III each of width $(B_2-B_1)/2=19.2$ mm in which there is only data of the wider detector B from one cardiac period in each case adjoins thereto on both sides. No better time resolution than half the rotation time is possible here. However, this is not critical in practice because with skillful placement of the entire scan volume of z width $2*B_2-(B_2-B_1)/2$, i.e. 133.4 mm in our example, the critical regions with pronounced movement, such as the exit of the right coronary artery, may in any case be located in a region in which there is data present from both detectors A and B.

In order to enlarge the scan volume in the z direction it is also possible to join together more than two sequence scans with the above-described overlap, such that the regions with optimized time resolution due to scanning with the wider detector B in two cardiac periods with a two-segment reconstruction and optimized time resolution due to simultaneous scanning with two detectors A and B in the same cardiac periods with a dual-source reconstruction alternate in each case.

Figure 2:
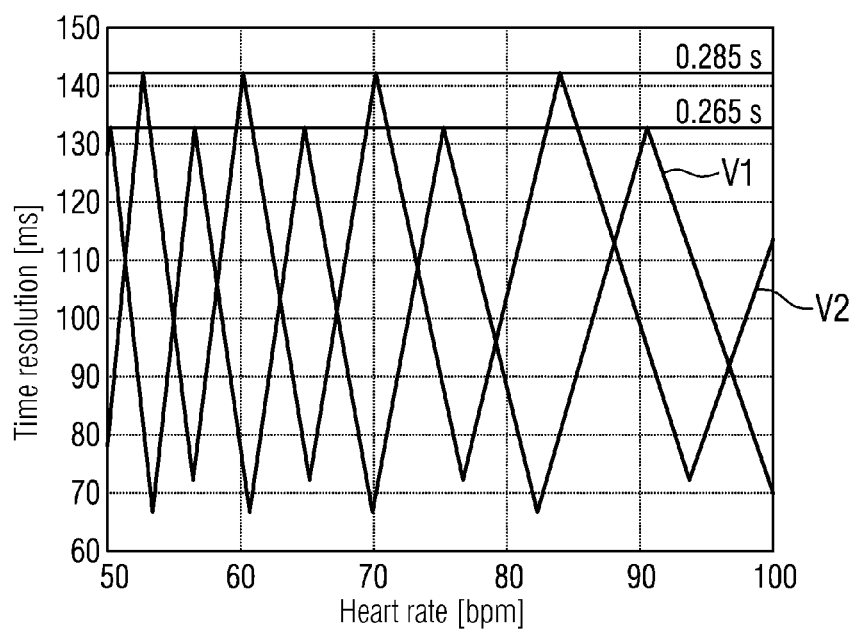
FIG. 2: shows a graph for optimized selection of the gantry rotation time relative to the heart rate for an ECG-triggered CT scan.

It is also possible to improve the time resolution in the region I of the two-segment reconstruction overlappingly scanned by the wide detector in that the patient's ECG is analyzed before the scan and the rotation time of the scanner is adjusted to the heart rate that is to be expected during the examination, for example following a test breathing command. FIG. 2 shows such a graph in which the time resolution in milliseconds is plotted on the ordinate against the present heart rate in beats per minute (=bpm) for two different rotational speeds of the gantry. The zigzag-shaped characteristic V1 is plotted in relation to the faster rotational speed at 0.265 s per revolution and the likewise zigzag-shaped characteristic V2 is plotted in relation to the slower rotational speed at 0.285 s per revolution. Both curves show a plurality of pronounced nested minima at which an optimum time resolution is given. Thus, a rotational speed can be selected in each case according to a present heart rate, at which speed an optimization of the time resolution with a two-segment reconstruction may be achieved.

Overall, therefore, a recording technology for ECG-triggered sequence scans for imaging the heart with a dual-source CT device with two detectors of different widths in z direction is described. With the new method the heart can be imaged with only two ECG-triggered axial scans in the case of a dual-source CT device with a detector that is sufficiently wide in the z direction and a detector that is at least half as wide in the z direction. The very good time resolution of a dual-source CT device or at least an optimized time resolution compared with a single-source CT device with the same rotation time is achieved in the central region of the examination volume.

Figure 3:
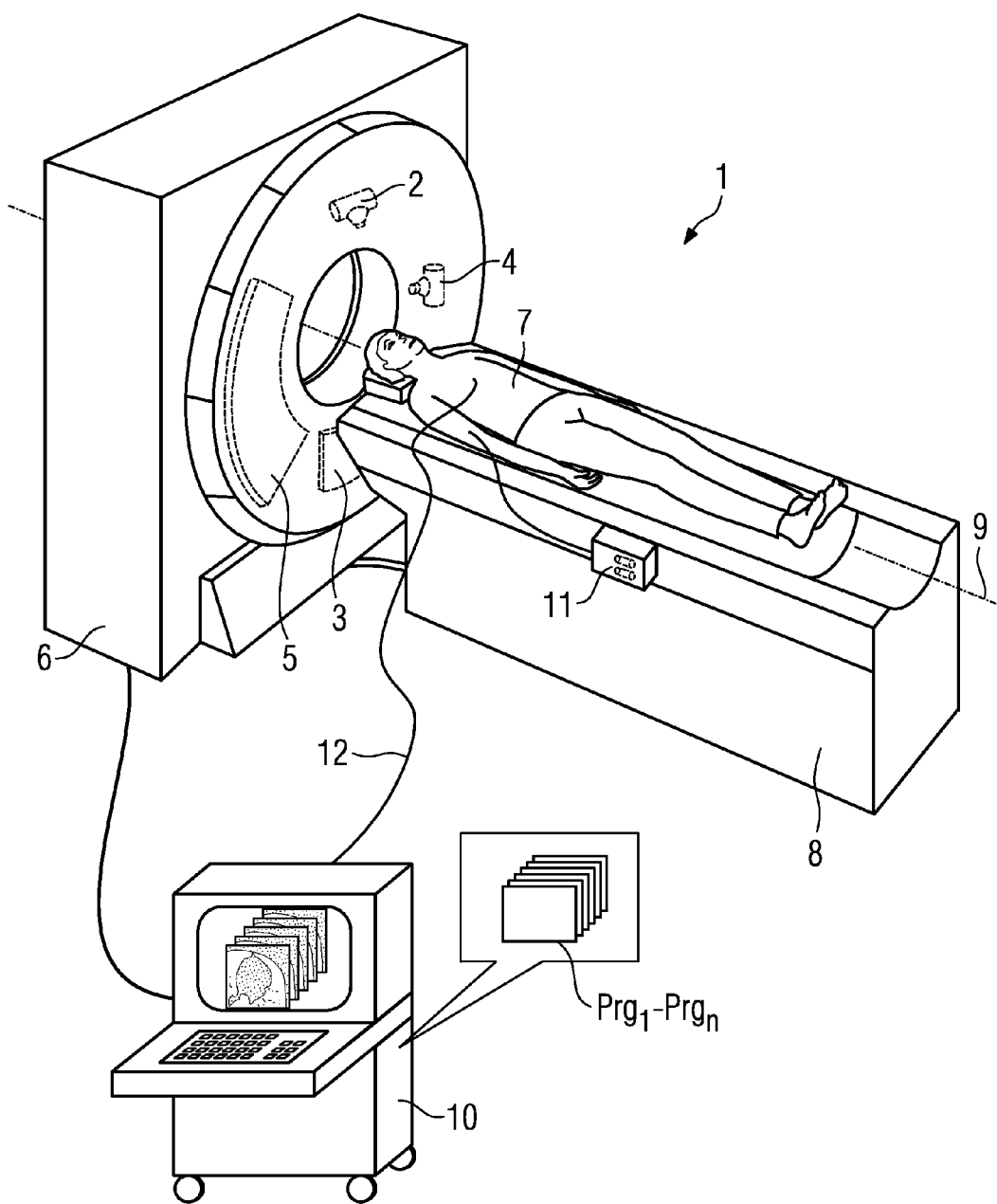
FIG. 3: shows a dual-source CT device.

Finally, FIG. 3 shows an example of an inventive dual-source CT device 1 with two focus-detector systems. The two focus-detector systems are formed by a first X-ray tube 2 with an oppositely disposed, relatively narrow detector 3 compared to the second detector 5, and by a second X-ray tube 4 with an oppositely disposed, relatively wide detector 5 in the system axis direction compared to the first detector 3. The two focus-detector systems are arranged angularly offset by 90° on the gantry and are located in the gantry housing 6. The patient 7, who is incrementally moved along the system axis 9 through the centrally arranged field of view in the course of the examination according to an embodiment of the invention, is located on the patient couch 8.

For ECG-triggered scanning an ECG evaluation is also provided in the computer 10 which with the aid of the ECG scan lead 12 attached to the patient can evaluate the ECG signals of the patient 7 and control the CT device accordingly. Also located on the patient couch 8 is a contrast agent applicator 11 which, controlled by the computer, can perform an appropriate contrast agent application as necessary.

The entire system is controlled by computer programs $Prg_1$-$Prg_n$ which are stored in a memory which can be accessed by the computer 10. Also contained in the memory is program code which can perform the inventive scanning and evaluation of the detector data including its reconstruction during operation of the system.

Overall, therefore, an embodiment of the invention presents a method for CT scanning a heart with a dual-source CT device having detectors of different widths in the system axis direction and reconstruction of tomographic image data, wherein at least two circular scans are performed at different z positions and the spacing in the z direction is chosen such that at least two first scan zones result which are scanned by means of a circular scan with two detectors and at least one second scan zone results which is scanned twice by one detector in two successive circular scans, a dual-source reconstruction being performed in the first scan zones and a two-segment reconstruction being performed in the at least one second scan zone and finally a common tomographic image data set being produced. An embodiment of the invention also describes a dual-source CT device in which the detectors have different widths in the system axis direction.

By way of addition attention is drawn to the fact that, owing to the desired high time resolution, the scans and image reconstructions described here relate predominantly to complete scans over an angular range of 180° plus fan angle (=180° scanning) and detector data from a projection interval of a total of 180° per image (=180° image) is accordingly used with the reconstructions.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

It is understood that the above-cited features of the invention can be used not only in the combination disclosed in each case, but also in other combinations or in isolation, without departing from the scope of the invention.

What is claimed is:

1. A method for CT scanning a heart with a dual-source CT device including two focus-detector systems with detectors of different widths in a system axis direction, and for reconstruction of tomographic image data, the method comprising:

performing at least two circular scans at different z positions, the spacing in the z direction being chosen such that at least two first scan zones are produced which are scanned by way of a circular scan with two detectors and at least one second scan zone being produced which is scanned twice by one detector in two successive circular scans;

reconstructing first tomographic image data in the at least two first scan zones using absorption data of a relatively narrower one of the two detectors and of a relatively wider one of the two detectors;

reconstructing second image data in the at least one second scan zone from absorption data of the relatively wider detector from two successive circular scans at different z positions; and assembling a common tomographic image data set from at least the reconstructed first and second image data.

2. The method as claimed in claim 1, wherein the CT scan is performed with ECG triggering.

3. The method as claimed in claim 1, wherein only detector data from a resting phase of the heart is used for the reconstruction.

4. The method as claimed in claim 1, wherein, as a function of an anticipated heart rate, a rotational speed is chosen which is time-resolution-optimized with respect to the reconstruction of second image data in the at least one second scan zone from absorption data of the relatively wider detector from two successive circular scans at different z positions.

5. The method as claimed in claim 1, wherein the relatively narrower detector is half as wide as the relatively wider detector.

6. The method as claimed in claim 1, wherein,
referring to the system axis direction, one or two marginal scan areas are present in which adequate scanning is performed with just one focus-detector system without changing the z position,
a reconstruction of an image data set is performed using detector data from a single sequence scan, and
said reconstructed image data is also added to the common tomographic image data set.

7. The method as claimed in claim 1, wherein the detectors are displaced relative to each other in the system axis direction between two successive circular scans.

8. A dual-source CT device comprising:
two focus-detector systems arranged on a gantry so as to be angularly offset, detectors of the two focus-detector systems including different widths in a system axis direction; and
a computer system including a program memory with program data being provided by which the dual-source CT device is controlled and CT image data is reconstructed during operation of the two focus-detector systems.

9. The dual-source CT device as claimed in claim 8, wherein the detectors of the two focus-detector systems are arranged on the gantry such that a relatively wider one of the detectors projects beyond a projection of a relatively narrower one of the detectors in the system axis direction to a same extent on either side of the projection of relatively narrower one of the detectors.

10. The dual-source CT device as claimed in claim 8, wherein the detectors are constructed so as to be displaceable relative to each other in the system axis direction.

11. A dual-source CT device comprising:
two focus-detector systems arranged on a gantry so as to be angularly offset, detectors of the two focus-detector systems including different widths in a system axis direction; and a computer system including a program memory with program data being provided by which the dual-source CT device is controlled and CT image data is reconstructed during operation of the two focus-detector systems, and wherein, a program code is stored in the program memory of the computer to perform the method as claimed in claim 1 when executed.

12. A tangible computer readable medium including program segments for, when executed on a computer device, causing the computer device to implement the method of claim 1.

13. The method as claimed in claim 2, wherein only detector data from a resting phase of the heart is used for the reconstruction.

14. The method as claimed in claim 3, wherein, as a function of an anticipated heart rate, a rotational speed is chosen which is time-resolution-optimized with respect to the reconstruction of second image data in the at least one second scan zone from absorption data of the relatively wider detector from two successive circular scans at different z positions.

* * * * *